(12) United States Patent
Koike et al.

(10) Patent No.: US 12,298,324 B2
(45) Date of Patent: May 13, 2025

(54) AUTOMATIC ANALYSIS APPARATUS AND CLEANING METHOD FOR SAME

(71) Applicant: Hitachi High-Tech Corporation, Tokyo (JP)

(72) Inventors: Misato Koike, Tokyo (JP); Masashi Akutsu, Tokyo (JP); Masashi Fukaya, Tokyo (JP); Megumi Kato, Tokyo (JP)

(73) Assignee: HITACHI HIGH-TECH CORPORATION, Tokyo (JP)

(*) Notice: Subject to any disclaimer, the term of this patent is extended or adjusted under 35 U.S.C. 154(b) by 892 days.

(21) Appl. No.: 17/601,087

(22) PCT Filed: Mar. 18, 2020

(86) PCT No.: PCT/JP2020/011972
§ 371 (c)(1),
(2) Date: Oct. 4, 2021

(87) PCT Pub. No.: WO2020/230451
PCT Pub. Date: Nov. 19, 2020

(65) Prior Publication Data
US 2022/0206029 A1    Jun. 30, 2022

(30) Foreign Application Priority Data

May 13, 2019  (JP) .................................. 2019-090500

(51) Int. Cl.
G01N 35/10    (2006.01)
G01N 33/48    (2006.01)
G01N 35/00    (2006.01)

(52) U.S. Cl.
CPC ......... G01N 35/1004 (2013.01); G01N 33/48 (2013.01); G01N 35/00693 (2013.01);
(Continued)

(58) Field of Classification Search
CPC .......... G01N 2035/0091; G01N 33/48; G01N 35/00693; G01N 35/00722; G01N 35/0092; G01N 35/1004
See application file for complete search history.

(56) References Cited

U.S. PATENT DOCUMENTS

2007/0175284 A1    8/2007  Oonum et al.
2012/0003731 A1*   1/2012  Kuroda ............ G01N 35/00732
                                                        134/18
(Continued)

FOREIGN PATENT DOCUMENTS

CN    107643410 A    1/2018
EP    2 930 517 A1   10/2015
(Continued)

OTHER PUBLICATIONS

Extended European Search Report received in corresponding European Application No. 20806124.2 dated Feb. 28, 2023.
International Search Report of PCT/JP2020/011972 Jun. 9, 2020.

*Primary Examiner* — Jennifer Wecker
(74) *Attorney, Agent, or Firm* — MATTINGLY & MALUR, PC (57) ABSTRACT

An automatic analysis apparatus includes: an automatic analysis unit 100 which includes a dispensing mechanism including a probe which is configured to dispense a sample or a reagent into a reaction container, a cleaning mechanism; and a control unit 124. The control unit includes a storage unit 124a configured to store count values which indicate weightings to contamination and are set in advance in accordance with a plurality of analysis conditions, a processing unit 124b configured to obtain a cumulative count for each dispensing of the sample or the reagent on the basis of the stored count values and to determine whether the obtained cumulative count exceeds a threshold value set in advance, and an instruction unit 124c configured to instruct (Continued)

an operation of the cleaning mechanism to clean the probe when a result of determination is that the cumulative count exceeds the threshold value.

24 Claims, 7 Drawing Sheets

(52) U.S. Cl.
CPC .................. *G01N 35/00722* (2013.01); *G01N 2035/0091* (2013.01)

(56)     References Cited

U.S. PATENT DOCUMENTS

| | | | |
|---|---|---|---|
| 2012/0048036 A1* | 3/2012 | Mimura | G01N 35/0092 |
| | | | 73/863.01 |
| 2014/0286824 A1* | 9/2014 | Yasui | G01N 35/04 |
| | | | 422/64 |
| 2015/0293135 A1 | 10/2015 | Yamashita et al. | |
| 2017/0003204 A1 | 1/2017 | Yamasaki et al. | |
| 2018/0128847 A1 | 5/2018 | Yasui et al. | |

FOREIGN PATENT DOCUMENTS

| | | |
|---|---|---|
| JP | 2007-225608 A | 6/2007 |
| JP | 2010-060550 A | 3/2010 |
| JP | 2016-003967 A | 1/2016 |
| WO | 2014/088004 A1 | 6/2014 |

\* cited by examiner

T : 1 CYCLE
S : DISPENSING SAMPLE
W : CLEANING

[FIG. 3B]

T : 1 CYCLE
S : DISPENSING SAMPLE
W : CLEANING

| ANALYSIS ITEM | COLORIMETRY | ISE | HbA1c |
|---|---|---|---|
| DISPENSING AMOUNT (CONTAMINATION RANGE INSIDE PROBE) | 1.0-25.0 μL | 10、15、20 μL | 1.3-2.0 μL |
| CONTAMINATION RANGE OUTSIDE PROBE | 2.25 mm | 2.25 mm | 55.0 mm |
| AN EXAMPLE OF ANALYTE TYPE | SERUM, PLASMA, URINE, SPINAL FLUID | SERUM, URINE | WHOLE BLOOD, BLOOD CELL |
| COUNT | 1 | 3 | 22.5 |

| ANALYSIS ITEM | COLORIMETRY | ISE | HbA1c |
|---|---|---|---|
| COUNT | 1 | 3 | 22.5 |

601

| DISPENSING OPERATION | SUCTION FROM LIQUID SURFACE OF SAMPLE CONTAINER | SUCTION FROM BOTTOM SURFACE OF SAMPLE CONTAINER |
|---|---|---|
| COUNT | 3 | 22.5 |

602

| DISPENSING AMOUNT | 1.0-5.0 μL | 5.0-15.0 μL | 15.1-25.0 μL |
|---|---|---|---|
| COUNT | 1 | 3 | 5 |

603

| ANALYTE TYPE | SERUM, PLASMA | URINE | SPINAL FLUID, WHOLE BLOOD, BLOOD CELL |
|---|---|---|---|
| COUNT | 3 | 1 | 22.5 |

604

| ALARM | ABNORMAL PRESSURE WAVEFORM WHEN SUCKING | SAMPLE CLOGGING HAPPENED |
|---|---|---|
| COUNT | 112.5 | 225 |

| CONDITION | MOST HIGHLY CONTAMINATED STATE OF SAMPLE PROBE IN CONSIDERATION OF CONDITIONS |
|---|---|
| ANALYTE TYPE | ANALYTE WITH HIGH VISCOSITY AND HIGH CONCENTRATION OF PROTEIN COMPONENTS (FOR EXAMPLE, WHOLE BLOOD) |
| INSIDE OF SAMPLE PROBE | IN ADDITION TO SAMPLE DISPENSING AMOUNT OF 25 μL, SUCK DUMMY AMOUNT OF 7.5 μL |
| OUTSIDE OF SAMPLE PROBE | DISPENSE FROM INNER BOTTOM OF SAMPLE CONTAINER TO HEIGHT OF 59 mm (SAMPLE PROBE IS CONTAMINATED BY 55 mm FROM LIQUID SURFACE) |

SET COUNT VALUE
☐ NO SET
☑ SET    PERFORM CLEANING [   ] COUNT

ANALYSIS ITEM   COLORIMETRY [   ] COUNT   HbA1c [   ] COUNT   ISE [   ] COUNT

ANALYTE TYPE   BLOOD   SERUM [   ] COUNT   PLASMA [   ] COUNT
              WHOLE BLOOD [   ] COUNT   BLOOD CELL [   ] COUNT
              URINE [   ] COUNT
              SPINAL FLUID [   ] COUNT

[UPDATE]  [SAVE]

AUTOMATIC ANALYSIS APPARATUS AND CLEANING METHOD FOR SAME

TECHNICAL FIELD

The present invention relates to an automatic analysis apparatus and a cleaning method for the same.

BACKGROUND ART

An automatic analysis apparatus is an apparatus that analyzes a biological sample (hereinafter, an analyte may be referred to as a sample) such as blood, urine, and spinal fluid. The automatic analysis apparatus has a function of dispensing, for example, each of the sample and a reagent from a respective one of preservation containers into a reaction container using a dispensing mechanism equipped with a probe for the sample and a probe for the reagent (hereinafter, referred to as a sample probe and a reagent probe), stirring a mixed solution of the sample and the reagent, then measuring a color tone change and reaction time of a reaction solution by a detector, quantifying a concentration, an activity value, or a reaction time of a target component in the sample based on measured data, and outputting a calculated result.

In such an automatic analysis apparatus, when the sample probe and the reagent probe repeat dispensing operations, in order to avoid carryover between the sample and the reagent, the probe is cleaned in preparation for a next dispensing operation after a target sample and a target reagent are discharged to the reaction container.

In recent years, it is desired that the automatic analysis apparatus is capable of performing various inspection items while having a small size at which the automatic analysis apparatus is capable of being introduced into a limited inspection space. In order to implement this automatic analysis apparatus, it is required to handle a plurality of samples and reagents by a single dispensing mechanism.

In particular, in a sample dispensing mechanism in which a plurality of contamination factors are assumed, for example, a sample dispensing mechanism in which a plurality of analyte types and a plurality of analysis items are dispensed by a single probe, a contamination state of the sample probe after dispensing varies depending on the analyte type and the analysis item, and accumulation states of contamination after the dispensing is performed a predetermined number of times are not always uniform. The same applies to a reagent dispensing mechanism in which a plurality of contamination factors are assumed, for example, a reagent dispensing mechanism in which a plurality of reagents or a plurality of analysis items are performed by a single probe. Further, the same also applies to a mechanism including a reaction container in which a plurality of contamination factors are assumed, for example, a reaction container in which a plurality of analyte types and a plurality of analysis items are handled in a single container.

However, the carryover between the sample and the reagent needs to be designed in a manner of falling within a range that does not cause a clinical problem. As for the reduction of the carryover in the sample dispensing mechanism, a method of weighting a suction amount and the number of times of dispensing and performing additional cleaning is known. PTL 1 describes a method of changing at least one of the number of times of cleaning or cleaning time when the probe is cleaned on the basis of at least one of the number of times of sampling of the analyte or a sampling amount of the analyte in the sample probe.

CITATION LIST

Patent Literature

PTL 1: Japanese Patent No. 2007-225608

SUMMARY OF INVENTION

Technical Problem

When the method in PTL 1 is adopted to execute a plurality of analyte types and a plurality of analysis items by a single sample dispensing mechanism, even when the number of times of sampling is equal, contamination states of a sample probe may be different. For example, based on characteristics of a sample such as components contained in the sample and the viscosity of the sample, the sample probe is more contaminated when a whole blood sample is dispensed 100 times than when a serum sample is dispensed 100 times. A sampling amount is a weighting to contamination inside the sample probe. However, for example, when a blood collection tube is used as a sample container, contamination outside the sample probe is larger when the sample is suctioned from a bottom surface of the container than when the sample is suctioned from a liquid surface. Therefore, in the weightings of stains based on the number of times of sampling and the sampling amount, the above reasons are insufficient for avoiding carryover when the plurality of analyte types, reagents, and the plurality of analysis items are handled by a single dispensing mechanism.

An object of the invention is to provide an automatic analysis apparatus and a cleaning method for the same that are capable of avoiding carryover and maintaining analysis performance in a dispensing mechanism or a reaction container in which a plurality of contamination factors are assumed.

Solution to Problem

In order to achieve the above-mentioned object, the invention provides an automatic analysis apparatus including: a dispensing mechanism including a probe configured to dispense a sample or a reagent into a reaction container; a cleaning mechanism configured to clean the probe; and a control unit configured to control the dispensing mechanism and the cleaning mechanism, in which the control unit obtains, on the basis of count values indicating weightings to contamination and corresponding to a plurality of analysis conditions, a cumulative count obtained by accumulating the count values for each dispensing of the sample or the reagent, and controls the cleaning mechanism to clean the probe when the cumulative count exceeds a set threshold value.

In order to achieve the above-mentioned object, the invention provides a cleaning method for the automatic analysis apparatus. The automatic analysis apparatus includes: a dispensing mechanism including a probe configured to dispense a sample or a reagent into a reaction container; a cleaning mechanism configured to clean the probe; and a control unit configured to control the dispensing mechanism and the cleaning mechanism. The control unit obtains, on the basis of count values indicating weightings to contamination and corresponding to a plurality of analysis conditions, a cumulative count obtained by accumulating the count values for each dispensing of the sample or the reagent, and controls the cleaning mechanism to clean the probe when the cumulative count exceeds a set threshold value.

Advantageous Effect

According to the invention, in a dispensing mechanism having a mechanism in which a plurality of contamination factors are assumed, it is possible to perform efficient cleaning in which the contamination factors suffered by the corresponding mechanism or contamination states during analysis are reflected.

DESCRIPTION OF EMBODIMENTS

Hereinafter, an embodiment of the invention will be described with reference to the drawings.

First Embodiment

A first embodiment is an embodiment of an automatic analysis apparatus and a cleaning method for the same. The automatic analysis apparatus includes: a dispensing mechanism including a probe configured to dispense a sample or a reagent into a reaction container; a cleaning mechanism configured to clean the probe; and a control unit configured to control the dispensing mechanism and the cleaning mechanism. The control unit obtains, on the basis of count values indicating weightings to contamination and corresponding to a plurality of analysis conditions, a cumulative count obtained by accumulating the count values for each dispensing of the sample or the reagent, and controls the cleaning mechanism to clean the probe when the cumulative count exceeds a set threshold value.

Figure 1:
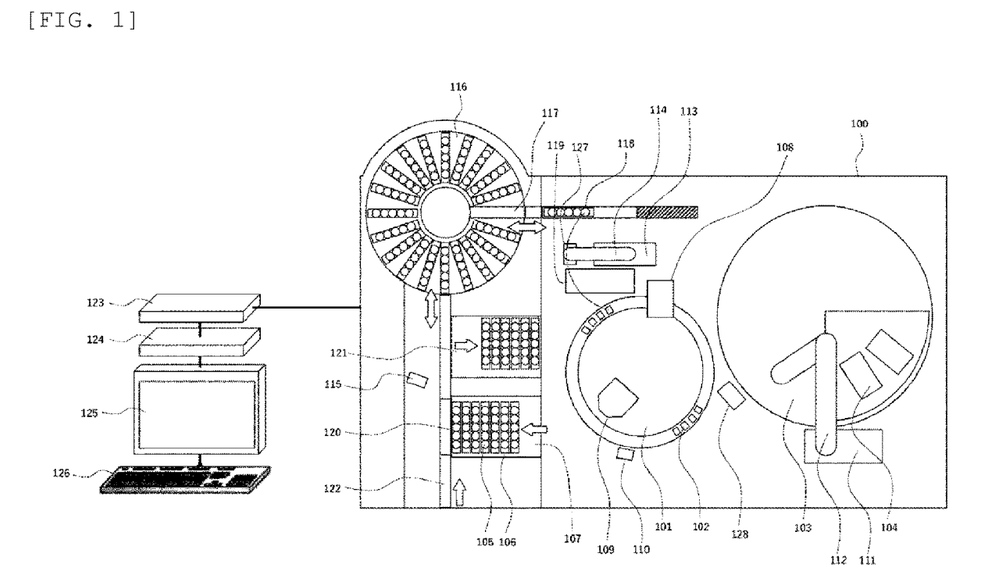
FIG. 1 is a schematic configuration diagram of an automatic analysis apparatus according to a first embodiment.

FIG. 1 is a view showing an example of a schematic configuration of the automatic analysis apparatus according to the present embodiment. The automatic analysis apparatus that dispenses a plurality of types of analytes includes a dispensing mechanism that suctions and discharges a plurality of types of liquids such as the sample or the reagent in order to measure a concentration, an activity value, or reaction time of a target component in a biological sample containing a plurality of components such as blood and urine, a reaction container that accommodates the sample and the reagent, and a cleaning mechanism.

In FIG. 1, reaction containers 102 are arranged in a cylindrical shape on a reaction disk 101. A plurality of reagent bottles 104 is capable of being arranged in a circular shape in a reagent disk 103. A sample transport mechanism 107 that moves racks 106 on which sample containers 105 are placed is provided near the reaction disk 101.

The reaction containers 102, a reaction container cleaning mechanism 108, a spectrophotometer 109, a stirring mechanism 110, the reagent disk 103, and the sample transport mechanism 107 are provided around the reaction disk 101, and a cleaning pump (not shown) is connected to the reaction container cleaning mechanism 108. Further, a reagent dispensing mechanism 111 that suctions the reagent from the reagent bottle 104 and discharges the reagent into the reaction container 102 is provided near the reaction disk 101 and the reagent disk 103. The reagent dispensing mechanism 111 includes a reagent dispensing probe (abbreviated as a reagent probe) 112.

A sample dispensing mechanism 113 that is capable of being rotated and moved up and down is provided between the reaction disk 101 and the sample transport mechanism 107, and the sample dispensing mechanism 113 includes a sample dispensing probe (abbreviated as a sample probe) 114. The sample probe 114 is moved while drawing an arc around a rotation axis of the sample dispensing mechanism 113, suctions the sample from the sample container 105, discharges the sample into the reaction container 102, and performs sample dispensing.

A liquid feeding pump 206 for the sample is connected to the sample dispensing mechanism 113, and a pump for the reagent (not shown) is connected to the reagent dispensing mechanism 111. A sample probe cleaning tank 127 is provided within an operation range of the sample dispensing mechanism 113, and a reagent probe cleaning tank 128 is provided within an operation range of the reagent dispensing mechanism 111.

The sample container 105 contains an inspection sample such as blood, is placed on the rack 106, and is carried by the sample transport mechanism 107. The sample dispensing mechanism 111 suctions the sample from the sample container 105 located at a sample suction position 118. Each mechanism is connected to a control unit 124 via an interface 123, and operations of each mechanism are controlled by the control unit 124. The control unit 124 receives inputs from an operation unit 125 and an operation input unit 126. The control unit 124 has a function as an analysis unit that analyzes the inspection sample in the reaction container 102.

In the present embodiment, the rack on which the sample container is placed is transported to the reagent suction position 118 by the sample transport mechanism 107 having a lane that transports the rack, but the same mechanism and operation as those according to the embodiment may not be used as long as a mechanism has the same object as the sample transport mechanism 107. For example, if there is a sample disk on which the sample container is provided, the sample container may be provided on the sample disk. For example, a sample transport mechanism that transports the rack using a rack arm capable of freely accessing the rack on which the sample container is placed may be used. In the present embodiment, the sample dispensing mechanism 113 is moved while drawing the arc around the rotation axis and suctions the sample, but the operation as in the embodiment may not be performed as long as a mechanism has the same object as the sample dispensing mechanism 113. For example, the sample dispensing mechanism may be a structure that has a sample dispensing arm capable of freely accessing a sample container side. FIG. 1 shows a stand-alone device of an automatic biochemical analysis apparatus, but a modular device may be used.

Figure 2:
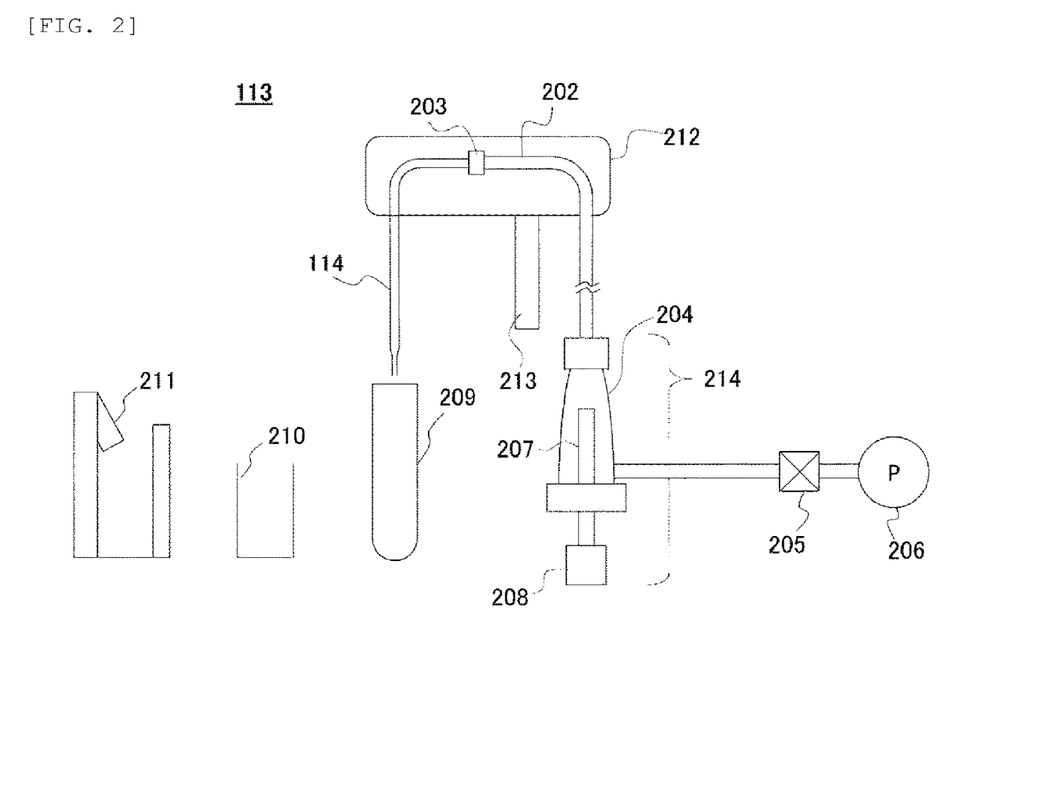
FIG. 2 is a schematic configuration diagram of a sample dispensing mechanism according to the first embodiment.

FIG. 2 is a schematic configuration diagram showing the sample dispensing mechanism 113 according to the first embodiment. In FIG. 2, the sample probe 114 that suctions and discharges the sample is capable of being moved up and down and rotationally moved by an arm 213, and the sample probe 114 is connected to a pipetter unit 214 that controls suction and discharge of the sample. Further, the sample dispensing mechanism 113 includes a pump 206 that supplies system water to a flow path from the pipetter unit 214 to the sample probe 114, a flow path that connects the pump 206 and the pipetter unit 214, and at least one electromagnetic valve 205 that is in the flow path and controls the flow of the system water. Cleaning water is stored in a tank (not shown). The reagent dispensing mechanism 111 and the sample dispensing mechanism 113 are not limited to a pipetter type device, and may be a drain type device.

Next, returning to FIG. 1, analysis operations of the automatic analysis apparatus according to the present embodiment will be described. The sample dispensing mechanism 113 suctions the sample from the sample container 105 on the rack 106 by the sample probe 114 and discharges the sample into the reaction container 102. The reagent dispensing mechanism 111 suctions the reagent from the reagent bottle 104 by the reagent probe 112 and discharges the reagent into the reaction container 102. The sample and the reagent that are dispensed into the same reaction container are mixed, and photometry of a mixed solution is executed by the spectrophotometer 109. The reaction disk 101 is rotated and stopped in one cycle, for example, 4.0 seconds, and photometry is periodically executed every time the reaction container 102 to be measured passes through the front of the spectrophotometer 109. After a certain period of time has elapsed, the control unit 124 calculates a concentration or an activity value of a target component in the sample on the basis of a photometry result of the spectrophotometer 109. The analysis is executed in this way.

Next, sample probe cleaning will be described. The sample dispensing mechanism 113 dispenses the sample from the sample container 105 that has arrived at the sample suction position 118 into the reaction container 102 using the sample probe once in one cycle, for example, 8.0 seconds, and repeats this cycle. Since a different sample may be dispensed after dispensing, the sample probe 114 is stopped at the sample probe cleaning tank 127 and is cleaned. That is, sample suction, sample discharge, probe cleaning, and sample suction are repeated sequentially for the sample probe 114, and the sample probe 114 is driven in one cycle from the sample suction to the next sample suction. Reagent suction, reagent discharge, the probe cleaning, and reagent suction are repeated sequentially for the reagent probe 112, and the reagent probe 112 is driven in the same manner as the sample probe in one cycle from the sample suction to the next sample suction, for example, 4.0 seconds.

Figure 3A:
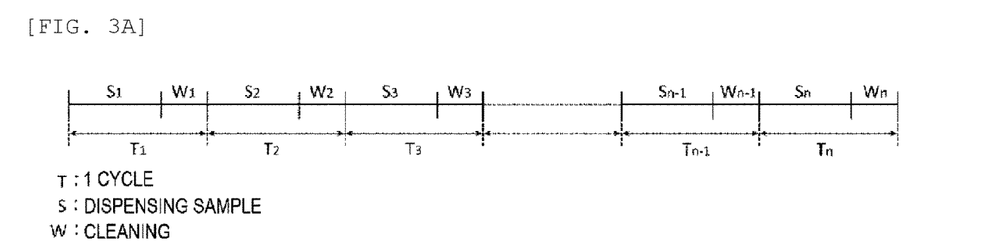
FIG. 3A is a diagram showing an example of a cycle of operations of the sample dispensing mechanism according to the first embodiment.
Figure 3B:
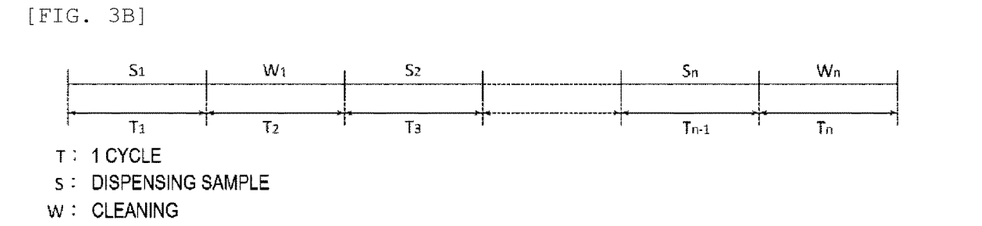
FIG. 3B is a diagram showing another example of the cycle of the operations of the sample dispensing mechanism according to the first embodiment.

In the present embodiment, as shown in FIG. 3A, the sample probe cleaning is included in one cycle of operations of the sample dispensing mechanism 113, and dispensing the sample from the sample container 105 into the sample container 102 using the sample probe 114 and cleaning the sample probe is set as one cycle, for example, 8.0 seconds. However, as shown in FIG. 3B, dispensing the sample from the sample container to the reaction container 102 using the sample probe 114 may be set as one cycle, and the sample probe cleaning may be performed in another cycle. Similarly, for the reagent dispensing mechanism 111, the reagent probe cleaning may be included in one cycle of operations of the reagent dispensing mechanism 111, and the reagent probe cleaning may be performed in a cycle separate from a cycle including reagent dispensing. In the present embodiment, water and a detergent are used as the cleaning water for the probe cleaning and reaction container cleaning, but only the water, only the detergent, or both the water and the detergent may be used. The detergent may be diluted. As a method for removing the contamination, for example, a cleaning operation for removing the contamination may be provided in the device in advance, or the user himself/herself may clean the device.

Figure 4:
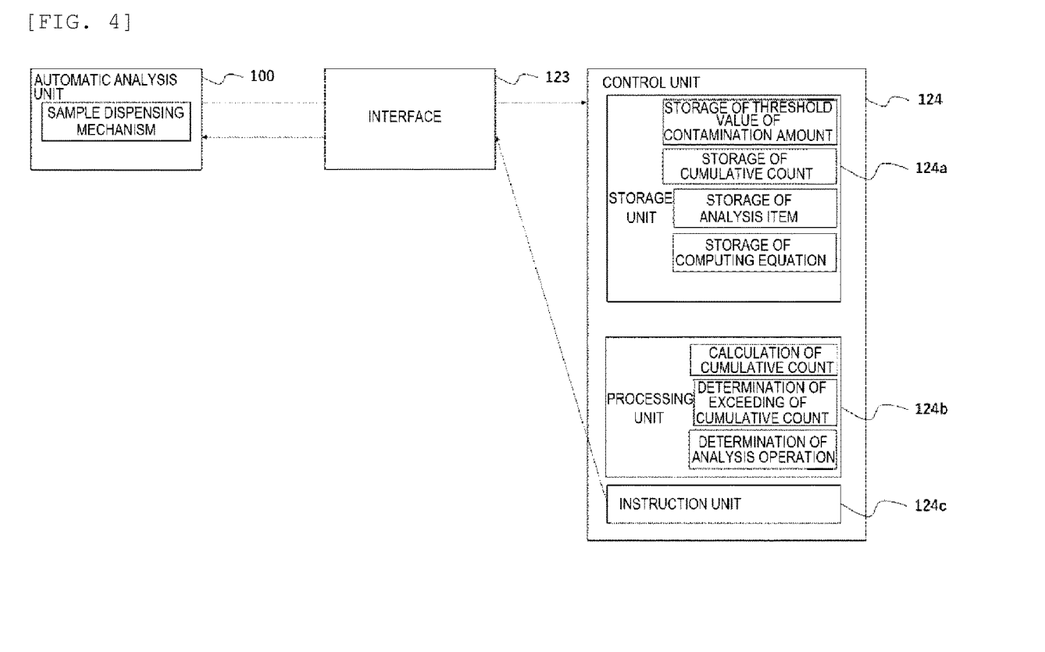
FIG. 4 is a specific configuration diagram of a control unit of the automatic analysis apparatus according to the first embodiment.

FIG. 4 is a specific configuration diagram showing the control unit 124 according to the first embodiment. The control unit 124 is, for example, a personal computer (PC), and includes a storage unit 124a, a processing unit 124b such as a central processing unit (CPU), an instruction unit 124c, and the like. The processing unit 124b of the control unit 124 executes an automatic analysis program stored in the storage unit 124a. The control unit 124 controls operations of the automatic analysis unit 100 including the sample dispensing mechanism via the interface according to sampling information.

Figure 5:
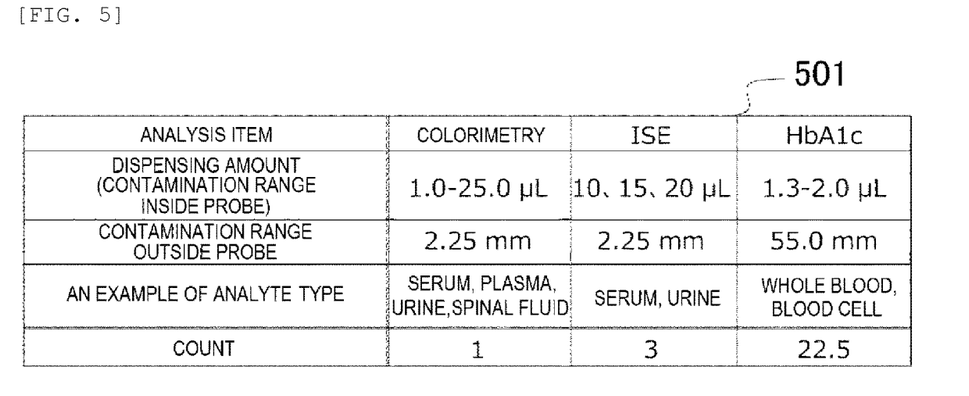
FIG. 5 is a diagram showing an example of count values indicating weightings of contamination according to the first embodiment.
Figure 6:
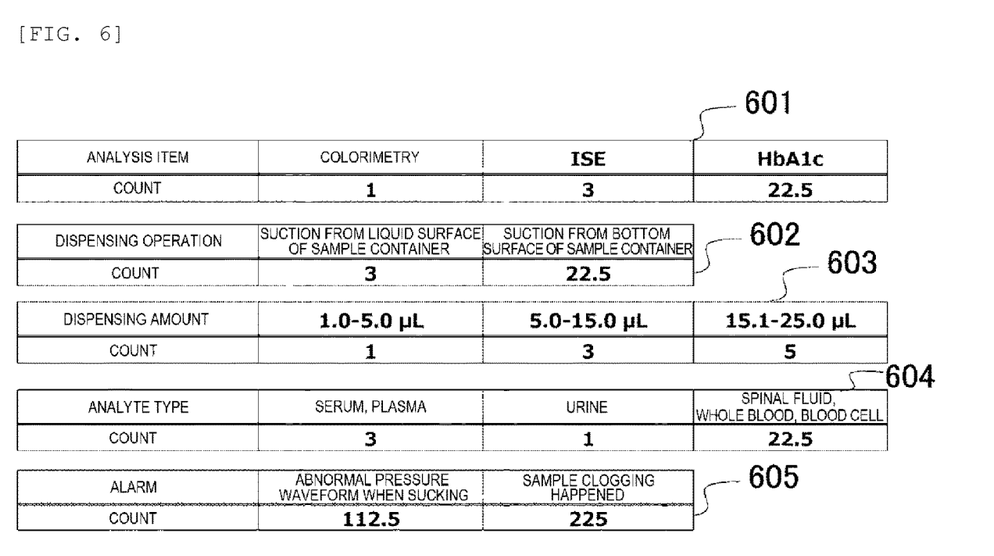
FIG. 6 is a diagram showing another example of the count values indicating the weightings of the contamination according to the first embodiment.

As shown in FIGS. 5 and 6, the storage unit 124a stores numerical values (hereinafter, referred to as count values) that indicate weightings to contamination and are set in advance according to a plurality of analysis conditions. Here, as shown in FIGS. 5 and 6, the analysis conditions mean analysis items, analyte types, dispensing amounts, and dispensing operations. Further, the storage unit 124a stores a cumulative count indicating accumulation of contamination amounts and a threshold value of the cumulative count for performing the contamination removing operation. In the present embodiment, the cumulative count of the probe is set to 0 in a state in which the contamination is not suffered or immediately after the cumulative count has exceeded the threshold value and the cleaning by the detergent which is the contamination removing operation has been performed. Further, the threshold value is set to 225 counts in consideration of a contamination state of the sample probe, a dispensing cycle of the sample probe, and the processing capability represented by the number of pieces of analysis processing per unit time of the device.

The storage unit 124a that stores a cumulative count of the current contamination amount performs a reset operation of the cumulative count when performing a sample probe cleaning work, for example, the cleaning by the detergent at operation start in the present embodiment, and stores the count as 0. Further, the storage unit 124a stores the analysis items that are analysis conditions. This is information set in advance on each of analytes that are sequentially transported from the sample transport mechanism 107 by a sample transport line 117. The information on each of the analytes is, for example, a name of a patient from whom the analyte is collected, the analyte types of the analyte such as serum or urine, the analysis items such as colorimetry, ISE, and HbA1c, and sampling amounts. Further, the storage unit 124a stores a computing equation used for calculating the contamination amount. The processing unit 124b calls and calculates values corresponding to the analysis items.

The control unit 124 compares the obtained cumulative count of the contamination amounts with the threshold value, and determines whether the cumulative count exceeds the threshold value. The device determines to execute the analysis continuously if the cumulative count does not exceed the threshold value. If the cumulative count exceeds the threshold value, the contamination removing operation is determined. The instruction unit 124c issues a content determined by the processing unit 124b to the sample dispensing mechanism of the automatic analysis unit via the interface 123.

Table 501 in FIG. 5 shows as a "count", in the automatic analysis apparatus according to the present embodiment, a dispensing amount, a range in which the sample probe is contaminated, and an example of the analyte type for each analysis item, and a count value of the analysis item that is obtained by comprehensively weighting the dispensing amount, the range in which the sample probe is contaminated, and the example of the analyte type for the analysis item. In the automatic analysis apparatus according to the present embodiment, the dispensing operation is determined based on the analyte type and the analysis item that are requested by the device. The analyte type represents the contamination amount that the sample probe suffers depending on components contained in the sample and characteristics of the sample such as the viscosity of the sample. In the present embodiment, the analysis items are classified into a colorimetry item, an ISE item, and an HbA1c item. Further, as for the analysis items, for example, the colorimetry item includes measurement items such as AST and LD. In the present embodiment, the colorimetry item and the HbA1c item are measured on the reaction disk 101, and the ISE item is measured on the ISE measurement unit 119.

The dispensing operation of the sample probe is determined based on the analyte type and the analysis item, and a suction amount of the sample and an immersion amount in the sample container change, and thus represent contamination ranges inside and outside the sample probe. In the present embodiment, the analysis items include the colorimetry, ISE, and HbA1c, but other analysis items such as immunity, coagulation, scattering, and MS may be used, for example. The contamination amount varies depending on each reaction principle or the characteristics of the reagent.

Reasons for setting the counts will be described while comparing the items. Regarding the analyte type, the viscosity of the analyte and a concentration of a contained protein component affect the contamination amount of the probe. In the present embodiment, in order to mainly analyze serum, plasma, urine, and whole blood, these analytes are compared. Since urine has a liquid property closer to that of the water and has a lower viscosity as relatively compared with serum and plasma, the contamination can be easily removed by probe cleaning. Most of contained components are metal ions and urea, and the adhesion of the protein component is small. On the other hand, whole blood contains components of red blood cells and white blood cells that are not contained in serum and plasma, and thus has a high viscosity. Concentrations of components such as iron and lactate dehydrogenase (LD), which are contained in large amounts in the blood cells, are high.

Therefore, the viscosity relatively increases in the order of urine, serum and plasma, and whole blood. The concentration of the protein component contained in the analyte that causes stains also increases in the order of urine, serum and plasma, and whole blood. Therefore, the contamination amount of the sample probe also increases in the order of urine, serum and plasma, and whole blood.

The contamination range outside the sample probe varies depending on the dispensing operation determined based on the analyte type and the analysis item. For example, in the present embodiment, when the sample is suctioned from the sample container, sampling in the colorimetry item and the ISE item is performed from a liquid surface of the sample based on the characteristics of the sample. At this time, the device performs a dispensing operation of suctioning the sample by lowering the liquid surface of the sample container by 2.25 mm after detecting the liquid surface of the sample container, that is, suctioning the sample at a position of 2.25 mm from the liquid surface. On the other hand, the sampling in the HbA1c item is performed from a bottom surface of the sample container based on the characteristics of the sample. At this time, when a height of the liquid surface of the sample is 59 mm from an inner bottom of the sample container, the device performs a dispensing operation of suctioning the sample from a position of 4 mm from the bottom surface of the sample container. That is, when the height of the sample is the highest, the device performs a dispensing operation of suctioning the sample by lowering the liquid surface of the sample container by 55 mm. Therefore, the contamination range outside the probe is wider in the HbA1c item than in the colorimetry item and the ISE item.

The contamination range inside the sample probe also varies depending on the dispensing operation determined by the analyte type and the analysis item. For example, when the sample is suctioned from the sample container, in the colorimetry item, a dispensing operation of additionally suctioning a dummy amount of 7.5 μL is performed in order to accurately dispense the sample in addition to being able to perform the dispensing of 1.0 μL to 25.0 μL. Therefore, the contamination inside the sample probe of 25.0 μL+the dummy amount of 7.5 μL occurs at the maximum. In the ISE item, the dispensing operation of additionally suctioning the dummy amount of 7.5 μL is performed in order to accurately dispense the sample in addition to being able to perform three patterns of dispensing of 10.0 μL, 15.0 μL, and 20.0 μL. Therefore, the contamination inside the sample probe of 20.0 μL+the dummy amount of 7.5 μL occurs at the maximum.

In the HbA1c item, a dispensing operation, called a water extrusion method, of discharging 1.3 μL to 2.0 μL of the dispensed sample together with the system water. Therefore, the contamination inside the sample probe of 2.0 μL occurs at the maximum. Therefore, the maximum contamination range inside the probe increases in the order of the HbA1c item, the ISE item, and the colorimetry item.

Although not shown in FIG. 5, a cleaning method for the sample probe is also considered. In the device according to the embodiment, the electromagnetic valve 205 in a sample probe flow path is opened in the sample probe cleaning tank, and the inside of the sample probe is cleaned by a strong water flow flowing in a thin probe. On the other hand, the outside of the reagent probe is cleaned by a sample probe cleaning mechanism 211 in the sample probe cleaning tank.

At this time, the cleaning water is applied from the side of the sample probe, but the water flow is weaker than that inside the sample probe. Therefore, when the sample probe is cleaned, it is more difficult to remove the stains on the outside by the cleaning than the stains on the inside.

As a result of comprehensively in consideration of the above, in the present embodiment, the count value that is the weighting to the contamination is set to 1 count for the colorimetry item, 3 counts for the ISE item, and 22.5 counts for the HbA1c item. When the weighting is executed, as shown in Table 501 in FIG. 5, one item may be decomposed into elements, and the weighting may be executed in consideration of all the elements.

As shown in Tables 601 to 605 in FIG. 6, final contamination counts may be given by weighting conditions of the analysis items, the dispensing operations, the dispensing amounts, the analyte types, and alarms and causing the device to execute a calculation. That is, for example, the storage unit has information on the count values for the conditions shown in Tables 601 to 605 in FIG. 6. Further, the storage unit stores a computing equation for multiplying the conditions shown in FIG. 6 to calculate the count values per time of sample dispensing.

It is assumed that the automatic analysis apparatus receives a request of the colorimetry item, a serum analyte, and a sample dispensing amount of 20 μL and starts the analysis in a state in which the cumulative count of the contamination of the probe is 0 counts. When the sample dispensing of the above-mentioned request is successful, the processing unit 124*b* calls information in FIG. 6 set in the storage unit 124*a* in advance, and sets the colorimetry to 1 count, serum to 3 counts, and the sample dispensing amount to 5 counts. Then, the processing unit 124*b* calculates these count values based on the computing equation of the storage unit 124*a*. For example, it is calculated that 1 count of the colorimetry×3 counts of the serum×5 counts of the sample dispensing amount=15 counts. Then, the storage unit adds 15 counts, which is the above-mentioned calculated value, and 0 counts, which is the cumulative count, and stores a new cumulative count of 15 counts.

It suffices as long as the count value, the threshold value, and the computing equation of the weighting of the stains are able to reflect the contamination status of the probe. Therefore, the count value, the threshold value, and the computing equation of the weighting of the stains may be stored in the storage unit in advance. Alternatively, depending on an actual usage situation, the user may execute a new setting by the operation input unit 126 or add a correction to each value in the storage unit.

For example, in the device, the contamination state, easiness of adhesion of the contamination, and easiness of removing vary depending on factors such as environmental conditions, maintenance frequency, and deterioration over time. Therefore, the setting of the count value in consideration of these factors and the correction of the threshold value and the cumulative count may be executed.

Figure 7:
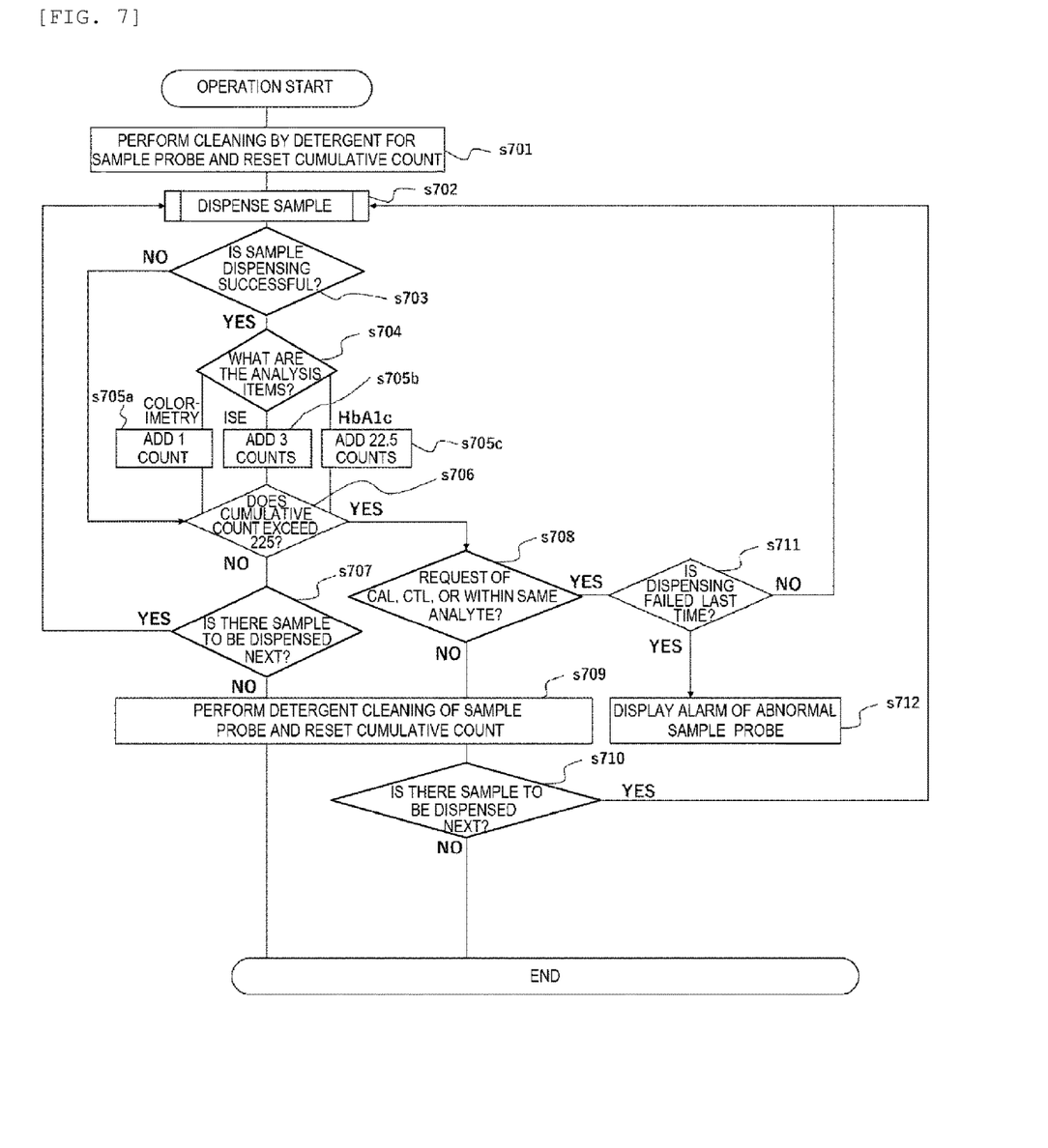
FIG. 7 is a diagram showing a flow chart related to weightings of contamination of a sample probe from operation start to end according to the first embodiment.

FIG. 7 is a flow chart related to the weightings of the contamination of the sample probe from operation start to end in the sample probe 114 according to the present embodiment. In the automatic analysis apparatus, when the operation is started, in the present embodiment, as a preparation operation for starting the analysis, the cleaning by the detergent for the sample probe is performed, and the cumulative count of the accumulated contamination is reset (s701).

In parallel with the above-mentioned operation, the sample is transported to the sample suction position 118 of the sample probe 114 via the sample transport mechanism 107 in FIG. 1, and the sample 1, which is serum, arrives at the sample suction position 118. When the sample arrives at the sample suction position 118, the device calls the storage of the analysis items requested in advance from the storage unit 124*a* of the control unit 124, and performs the sample dispensing. After the sample dispensing, in the present embodiment, it is determined whether the sample dispensing is successful based on, for example, information of liquid surface detection by a liquid surface sensor, a pressure waveform at the time of sample suction, and clogging detection (s703). If the dispensing is successful, the process proceeds to step s703. If the dispensing fails, the process returns to s702, the sample dispensing is performed again, and the determination in s703 is executed. If the sample dispensing fails again, in the present embodiment, the dispensing of the corresponding sample is stopped, the failure of the sample dispensing is stored in the storage unit, the count value is not calculated, and the process proceeds to the next sample dispensing.

If the sample dispensing is successful, the process proceeds to step s704 to determine the analysis item. The device calls information of the analysis item from the storage unit, and classifies the analysis item into any one of the colorimetry, ISE, and HbA1c in the present embodiment. Then, in the case of the colorimetry item, the processing unit of the control unit 124 adds 1 count to the cumulative count (s705*a*). Similarly, 3 counts are added in the case of ISE (s705*b*), and 22.5 counts are added in the case of HbA1c (s705*c*).

Next, the processing unit of the control unit 124 determines whether the cumulative count exceeds the threshold value. In the present embodiment, since the threshold value is set to 225 counts, it is determined whether the cumulative count exceeds 225 counts (s706). If the cumulative count does not exceed 225 counts, the process proceeds to step s707 to determine whether there is a sample to be dispensed next. If there is a sample to be dispensed next, the next sample dispensing is performed (s702). If there is no sample to be dispensed next, in the present embodiment, the cleaning by the detergent for the sample probe is performed before the end of the operation, the cumulative count is reset (s709), and the operation ends.

If the cumulative count exceeds 225 counts, in step s708, it is determined whether the sample dispensing for the corresponding sample is sample dispensing according to a request of a calibration (CAL) for correction, a request of a control (CTL) that is a measurement for accuracy management, or a request within the same analyte.

If the sample dispensing for the corresponding sample is not sample dispensing according to the request of the calibration, the request of the control, or the request within the same analyte, the cleaning by the detergent for the sample probe is performed, and the cumulative count is reset (s709). Next, the process proceeds to step s710 to determine whether there is a sample to be dispensed next. If there is a sample to be dispensed next, the sample dispensing is continuously performed (s702). If there is no sample to be dispensed next, the operation ends.

If the sample dispensing for the corresponding sample is sample dispensing according to the request of the calibration, the request of the control, or the request within the same analyte in step s708, in the present embodiment, the cumulative count exceeds 225 counts. However, the threshold value of 225 counts is a threshold value that is set with a margin for the contamination state that is considered to cause carryover. Therefore, if the cleaning by the detergent for the sample probe is performed, priority is given to preventing a risk of a change in analysis performance due to a change in a state of the sample probe before and after the cleaning by the detergent, and the control unit 124 executes control such that the sample dispensing continues until the sample dispensing according to the request of the calibration, the request of the control, or the request within the same analyte ends and the cleaning by the detergent for the sample probe is performed after the dispensing ends.

In the present embodiment, when the device determines that the sample dispensing fails, the count value received by the sample probe in the corresponding sample dispensing is not added to the cumulative count. However, the sample probe may also be contaminated by the sample when the sample dispensing fails. For example, a case is listed in which the liquid surface of the sample is detected and the sample suction is started, but there are bubbles in a sample solution and the device determines that the sample suction is not performed.

Therefore, even if the device determines that the sample dispensing fails, the count value may be added to the cumulative count. At that time, a method of adding the count value to the cumulative count may be changed based on a reason for determining that the sample dispensing fails. For example, there are bubbles on the liquid surface of the sample probe, liquid surfaces of liquid films of the bubbles are detected, and the sample probe starts the sample suction, but the sample is not capable of being suctioned, and the sample dispensing fails. In this case, since the contamination suffered by the sample probe from the sample is less than the suffered contamination when the dispensing is successful, the count value may be smaller than a count value planned to be added when the dispensing is successful. That is, when the colorimetry item is analyzed, if an example of adding 1 count to the cumulative count when the dispensing is successful is listed, it may be set, when the dispensing fails, to multiply the count value when the dispensing is successful by 0.5 and add an obtained value to the count value, and when the dispensing fails, 1 count×0.5=0.5 count may be added to the cumulative count.

An example of a method of calculating the count value when the dispensing fails will be described. If the dispensing fails (NO at s703), the process proceeds to s706 to determine whether the cumulative count of the sample probe exceeds 225. If the cumulative count does not exceed 225, the process proceeds to s707. If there is a sample to be dispensed next, the process proceeds to s702 to perform the sample dispensing again. If there is no sample to be dispensed next, the process proceeds to s709 to perform the cleaning of the sample probe and to reset the cumulative count.

On the other hand, if the cumulative count exceeds 225 counts in s706, the process proceeds to s708. If the sample dispensing for the corresponding sample is not sample dispensing according to the request of the calibration, the request of the control, or the request within the same analyte, the process proceeds to s709 to perform the cleaning of the sample probe and to reset the cumulative count. Regarding the calibration, the control, or the same analyte, since the states of the sample probe are different, measurement results may be different. Therefore, if the sample dispensing for the corresponding sample is sample dispensing according to the request of the calibration, the request of the control, or the request within the same analyte, the process proceeds to s711.

If the previous dispensing is successful in s711, since an abnormality may be caused by a factor other than the probe, for example, the liquid surface is not capable of being normally checked due to the bubbles adhering to the surface of the sample, the sample dispensing is performed again. On the other hand, if the previous dispensing also fails, the clogging of the probe may occur, for example, due to significant contamination of the probe by the sample. Since it is difficult to continue the analysis in the above-mentioned state, in the present embodiment, an alarm for the abnormality of the sample probe is displayed to notify a user of the abnormality of the device (s712).

In the present embodiment, the cumulative count is calculated after the sample dispensing has been successful, but the cumulative count may not be calculated after the sample dispensing has been successful. For example, if the requested item is in the storage unit of the device before the start of the analysis, the cumulative count may be calculated at the time when the analysis item is requested, and the analysis may be started after a cleaning timing of the sample probe has been scheduled in advance. When a state of the device changes with respect to a planned operation after the sample dispensing, for example, when the alarm occurs at the time of the sample dispensing or when the operation is not capable of being continued due to lack of the detergent or the reagent, it may be determined whether to change the calculation of the cumulative count as necessary.

Figure 8:
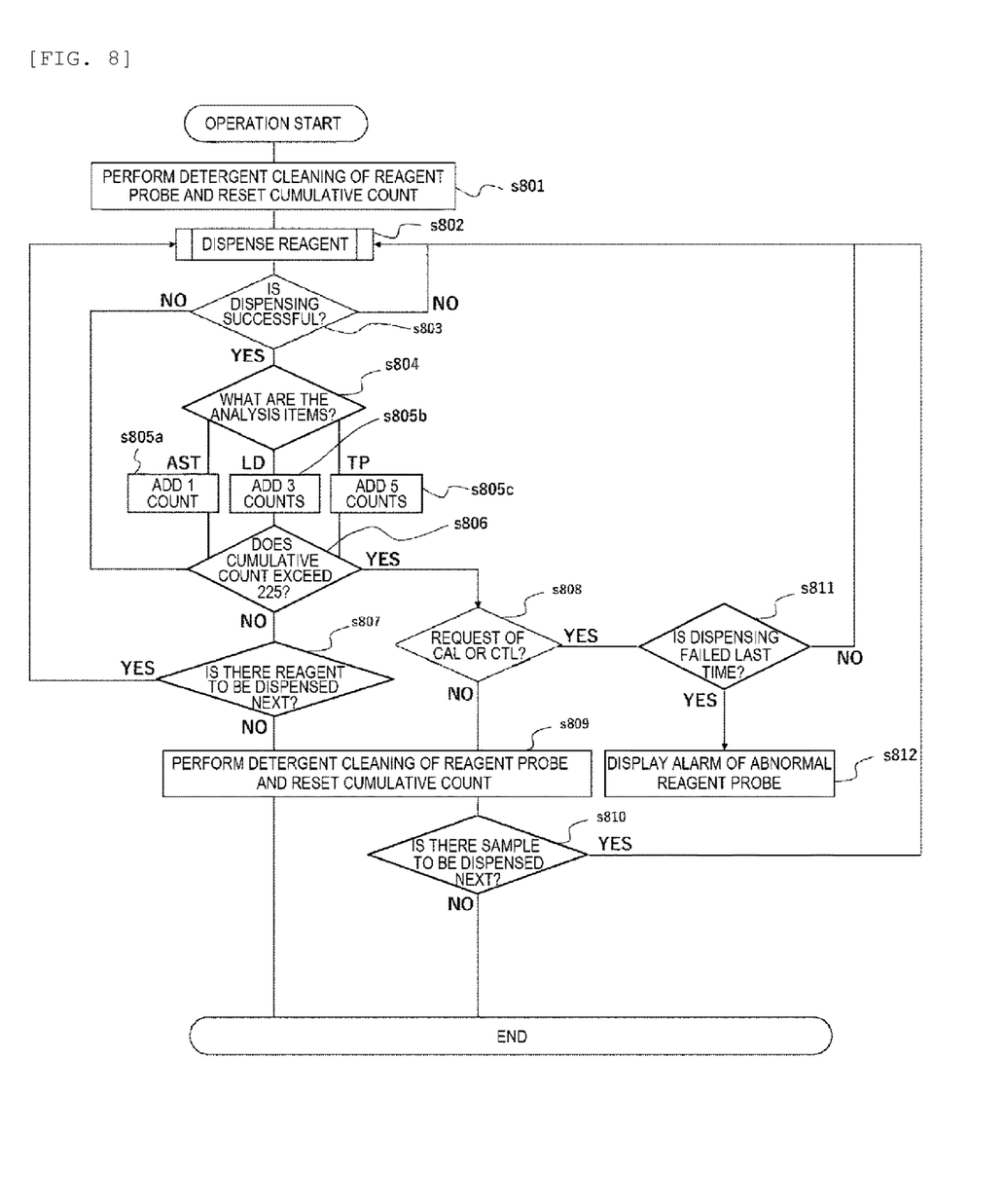
FIG. 8 is a diagram showing a flow chart related to weightings of contamination of a reagent probe from operation start to end according to the first embodiment.

FIG. 8 is a flow chart related to the weightings of the contamination of the reagent probe 112 from operation start to end in the sample probe 112. A basic determination flow is the same as that in FIG. 7. After the cleaning by the detergent at the operation start has been performed, the reagent probe 112 starts the reagent dispensing after checking success of the sample dispensing. In step s805, the reagent probe 112 determines the measurement items stored in the storage unit 124*a* of the control unit 124 for each reagent.

For example, when the reagent for AST, which is the colorimetry item, is dispensed, 1 count, which is the count value of the AST, is added to the cumulative count. In step s808, if the cleaning by the detergent for the reagent probe 112 is performed at the time of measuring analytes for the calibration (CAL) and the control (CTL), the priority is given to preventing the risk of the change in analysis performance due to the change in the state of the sample probe 112 before and after the cleaning by the detergent, and the control unit 124 executes control such that the sample dispensing continues until the reagent dispensing for the calibration and the control ends and the cleaning by the detergent for the sample probe 112 is performed after the dispensing ends.

Figure 9:
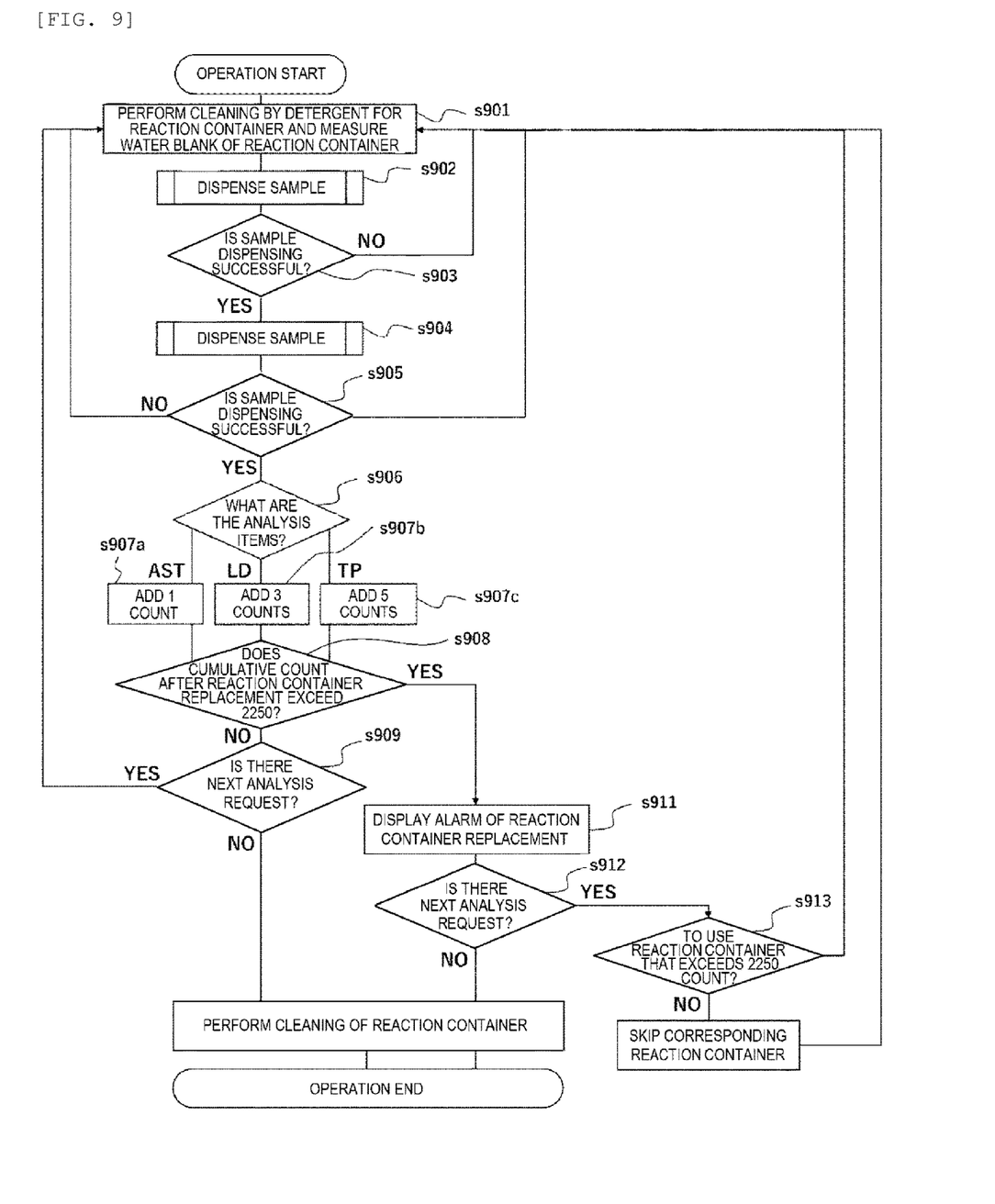
FIG. 9 is a diagram showing a flowchart related to weightings of contamination of a reaction container from operation start to end according to the first embodiment.

FIG. 9 is a flow chart related to the weightings of the contamination of the reaction container from operation start to end in the reaction container 102. When the operation is started, the automatic analysis apparatus according to the present embodiment performs the cleaning by the detergent for the reaction container 102 after the reset operation of each mechanism, and performs water blank measurements for the reaction containers in order from the reaction container 102 for which the cleaning ends. In the water blank measurement for the reaction container 102, water blank is measured three times in the present device, and when absorbance is significantly different from that in a measurement result of the water blank of the reaction container obtained in advance, it is determined that there is an abnormality in the reaction container 102 and a "reaction container skip" operation of not using the corresponding reaction container 102 is performed. When it is determined that there is no abnormality by comparing measurement results of the water blank of the reaction container 102 with the measurement result of the water blank of the reaction container obtained in advance, the operation of the sample dispensing is performed on the basis of the request for the analysis in the storage unit 124a of the control unit 124 (s902).

Thereafter, it is determined whether the sample dispensing is successful (s903). If the sample dispensing fails, the cleaning by the detergent for the reaction container 102 is performed for the reaction container 102 used when the above-mentioned sample dispensing fails until the water blank measurement of the reaction container 102 is performed, and a second time of sample dispensing is performed for another reaction container in which it is determined that there is no abnormality. If the sample dispensing is successful, the reagent dispensing is performed on the basis of the request for the analysis in the storage unit 124a of the control unit 124 (s904). Then, it is determined whether the reagent dispensing is successful (s905). If the reagent dispensing fails, the cleaning by the detergent for the reaction container 102 is performed for the reaction container 102 used when the reagent dispensing fails until the water blank measurement for the reaction container 102 is performed, and the second time of sample dispensing is performed for another reaction container 102 in which it is determined that there is no abnormality.

If the reagent dispensing is successful, the process proceeds to step s906 to determine the measurement item. The analysis item is called from the storage unit 124a of the control unit 124, and the count value corresponding to the item analyzed in the corresponding reaction container 102 is added to the cumulative count calculated and stored for each reaction container 102. For example, if a cumulative count of a reaction container 1 is 3 and the AST is analyzed in the reaction container 1, a count value 1 of the AST is added to the cumulative count 3 in accordance with step s907, and the cumulative count of the reaction container 102 is set to 4.

In the above-mentioned method, the count value is set in the measurement item, but the count value may be set in the analysis item. For example, serum of the analyte type (1 count), the AST of the measurement item (1 count), and the reaction time of 10 minutes (1 count) may be set, for example, serum×AST×reaction time=1×1×1=1 or serum+ AST+reaction time=1+1+1=3 may be satisfied.

Next, the process proceeds to step s908, and it is determined whether the cumulative count after replacement of the reaction container exceeds 2250. If the cumulative count does not exceed 2250, the process proceeds to step s909, and it is determined whether there is a next analysis item. If there is a next analysis item, the process proceeds to step s901 to perform the cleaning by the detergent for the reaction container and to prepare for a next analysis. If there is no next analysis item, the cleaning by the detergent for the reaction container is performed, and the operation ends.

If the cumulative count after the replacement of the reaction container exceeds 2250, it is notified to the user that the accumulation of the contamination may affect the analysis. For example, an alarm for the replacement of the reaction container is displayed (s911). Then, the process proceeds to step s912 to determine whether there is a next analysis request. If there is no analysis request, the reaction container is cleaned, and the operation ends.

If there is a next analysis request, it is determined whether to use a reaction container in which the cumulative count exceeds 2250 (s913). For example, when the user previously executes setting to skip the corresponding reaction container and to continue the analysis in setting, the corresponding reaction container is not used and is skipped, and the analysis is continued using a reaction container in which the cumulative count does not exceed 2250. For example, when maintenance of the replacement of the reaction container is set to be performed, the operation may be stopped so that the reaction vessel can be replaced. When there is a problem that the number of the reaction containers that can be used is reduced and the processing capability of the device is reduced if the reaction container in which the cumulative count exceeds 2250 is skipped, even when the cumulative count exceeds 2250, the reaction container in which the cumulative count is exceeded may be used for a short period of time, and an alarm that prompts the replacement of the reaction container may be issued at the end of the operation.

As a supplement, the contamination amount of the reagent probe or a reaction cell varies depending on the characteristics of the reagent to be handled by the device. For example, depending on characteristics of a modification site of a protein contained in the reagent, the contamination may be easily adsorbed on a specific material. Therefore, it is possible to avoid the carryover by weighting the contamination amount for the reagent probe or the reaction cell and performing appropriate cleaning or replacement of the reaction cell.

Figure 10:
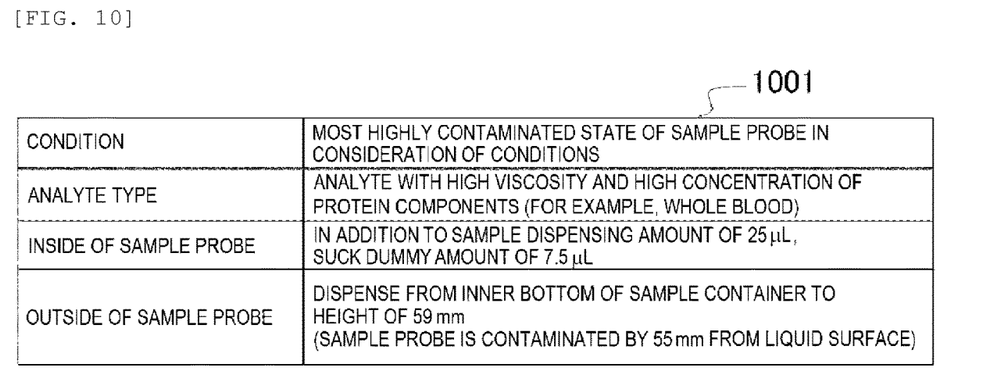
FIG. 10 is a diagram showing an example of a state in which the sample probe is most highly contaminated according to the first embodiment.

FIG. 10 is a diagram in which the contamination suffered by the sample probe 114 is assumed in the present embodiment. In the present embodiment, when the cumulative count exceeds 225, cleaning for avoiding the carryover in the sample probe is performed during the operation. The cleaning for avoiding the carryover in the sample probe is an operation for removing the maximum contamination suffered by the sample probe 114. The maximum contamination is determined in consideration of the analyte type to be handled by the sample probe and the contamination range of the sample probe 114. In the present embodiment, the sample probe 114 performs the analyte types shown in FIG. 5 and the dispensing operations in the analysis items shown in FIG. 5.

Table 1001 in FIG. 10 shows a state in which the sample probe 114 is most highly contaminated as considered based on FIG. 5. The analyte type has a high viscosity and has a high concentration of the protein component, for example, whole blood has the highest viscosity and the highest concentration of the protein component among serum, plasma, urine, and whole blood. The contamination range inside the sample probe becomes the maximum range when the analysis item is the colorimetry, the sample suction amount is 25 µL, and the dummy suction amount is 7.5 µL. The contamination range outside the sample probe becomes the maximum range when the analysis item is HbA1c and the analyte is dispensed to a height of 59 mm from the inner bottom of the sample container. Therefore, the cleaning by the detergent is performed in a cleaning operation in which the above-mentioned contamination is assumed to be removed. Accordingly, it is possible to deal with all contamination states that occur during the operation in one cleaning operation.

In the present embodiment, the analyte type is set on analysis parameters in advance and is not capable of being changed. However, the analyte that is not capable of being selected on the device may be set assuming a state in which the sample probe is most highly contaminated. The state may be considered with respect to the threshold value. For example, when it is desired to analyze the ascites but there is no ascites in options of the analyte type, an analyte type "others" may be set, and 22.5 counts may be set in one time of dispensing.

It is also possible to devise the cleaning operation, but in an automatic analysis apparatus that handles a plurality of analytes and reagents by a single dispensing mechanism, it is preferable to devise the count value rather than changing the cleaning. The setting of the count value may be stored in the storage unit by a designer of the device in advance or may be executed by the user on the operation unit 125.

Figure 11:
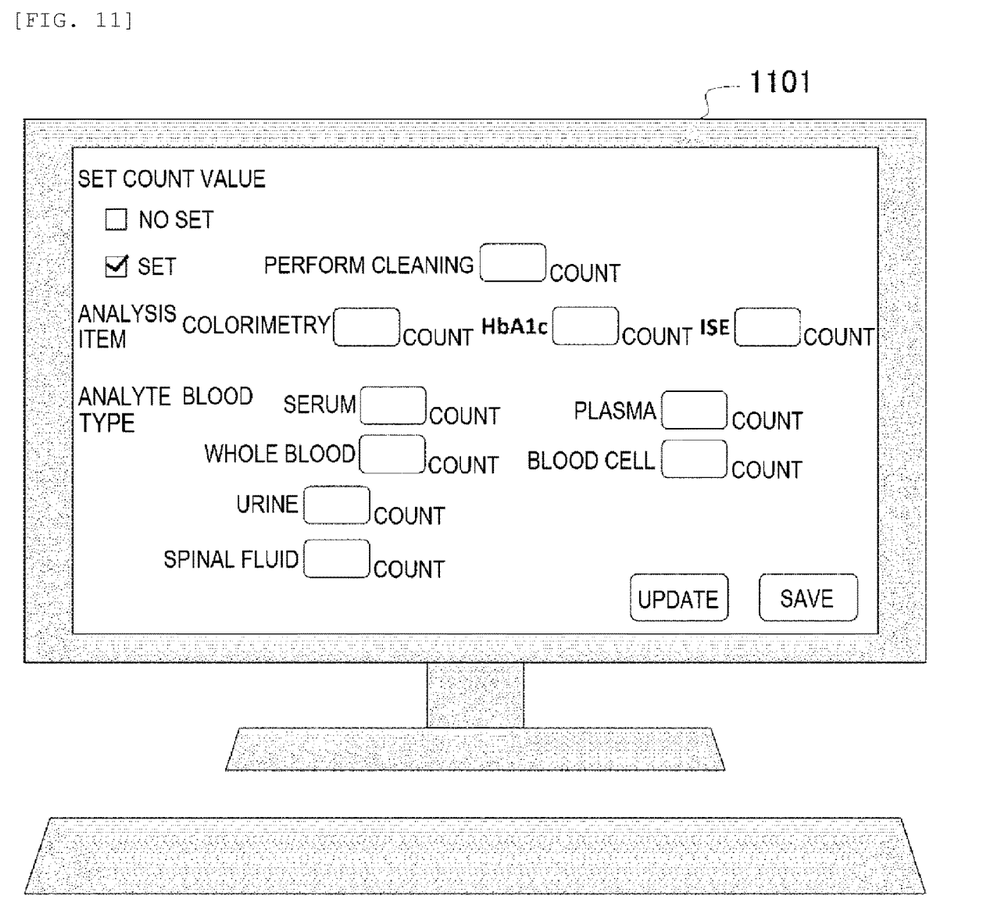
FIG. 11 is a diagram showing an example of a graphical user interface (GUI) when a user sets the count vales on an operation unit according to the first embodiment.

FIG. 11 shows an example of the operation unit (hereinafter, referred to as GUI) when the user sets the count value on the operation unit. When the user desires to set the count value of the contamination amount, the user displays a screen for setting the count value on the GUI, and inputs the count value to be set. On a screen 1101 that allows the count value to be set, for example, as shown in FIG. 11, the presence or absence of the setting of the count value can be selected. When the user selects setting, that is, when "select" is checked in FIG. 11, the count value can be input. That is, the control unit 124 is capable of using a count value set by the GUI that is capable of setting the count value instead of the count value set and stored in the storage unit 124a in advance.

The count value can be set for, for example, performing of the cleaning, the analysis item, and the analyte type. In the performing of the cleaning, a cumulative count value for performing the cleaning is capable of being set. Regarding the analysis item, the count value per time of dispensing is capable of being set for, for example, the colorimetry, HbA1c, and ISE. Regarding the analyte type, the count value per time of dispensing is capable of being set for, for example, blood, urine, and spinal fluid. Since the blood is an analyte that is often used in clinical inspection, the GUI that is capable of setting the count value in more detail is shown as an example.

The count value may be input, for example, by the user from the operation unit such as a keyboard on which a numerical value is capable of being input. The numerical value that is capable of being input on the GUI is stored in advance in the control unit 124, and the user may select a command from pull-down commands on the GUI and input the selected command, for example.

The invention is not limited to the embodiment described above and includes various modifications. For example, the above-mentioned embodiment has been described in detail for better understanding of the invention, and the invention is not necessarily limited to that including all configurations described above.

Further, although an example of creating a program for implementing a part or all of the above-mentioned configurations, functions, and control unit is mainly described, it is needless to say that a part or all of the above-mentioned configurations, functions, and control may be implemented by hardware, for example, by being designed with an integrated circuit. That is, all or a part of the functions of the control unit may be implemented by an integrated circuit such as an application specific integrated circuit (ASIC) or a field programmable gate array (FPGA), for example, instead of an operation program of the processing unit 124b.

REFERENCE SIGN LIST

100 Automatic analysis unit
101 Reaction disk
102 Reaction container
103 Reagent disk
104 Reagent bottle
105 Sample container
106 Rack
107 Sample transport mechanism
108 Reaction container cleaning mechanism
109 Spectrophotometer
110 Stirring mechanism
111 Reagent dispensing mechanism
112 Reagent dispensing probe (reagent probe)
113 Sample dispensing mechanism
114 Sample dispensing probe (sample probe)
115 Barcode reader
116 Rack rotor
117 Sample transport line
118 Sample suction position
119 ISE measurement unit
120 Rack supply unit
121 Rack housing unit
122 Emergency rack input unit
123 Interface
124 Control unit
125 Operation unit
126 Operation input unit
127 Sample probe cleaning tank
128 Reagent probe cleaning tank
202 Tube
203 Connection unit
204 Syringe
205 Electromagnetic valve
206 Liquid feeding pump
207 Plunger
208 Motor
209 Sample container
210 Reaction container
211 Sample probe cleaning mechanism
212 Cover
213 Arm
214 Pipetter unit

The invention claimed is:

1. An automatic analysis apparatus comprising: a dispensing mechanism including a probe configured to dispense a sample or a reagent into a reaction container; a cleaning mechanism configured to clean the probe; and a control unit configured to control the dispensing mechanism and the cleaning mechanism, wherein the control unit is programmed to obtain, on the basis of count values indicating weightings to contamination and corresponding to a plurality of analysis conditions, a cumulative count obtained by accumulating the count values for each dispensing of the sample or the reagent, where the analysis conditions include information on contamination ranges both inside and outside the probe, and controls the cleaning mechanism to clean the probe when the cumulative count exceeds a set threshold value.

2. The automatic analysis apparatus according to claim 1, wherein the analysis conditions include a dispensing operation.

3. The automatic analysis apparatus according to claim 2, wherein the analysis item includes colorimetry, ISE, and HbA1c.

4. The automatic analysis apparatus according to claim 2, wherein the analyte type includes serum, plasma, urine, spinal fluid, whole blood and blood cells.

5. The automatic analysis apparatus according to claim 2, wherein the dispensing operation includes suction from a liquid surface or a bottom surface of a sample container.

6. The automatic analysis apparatus according to claim 1, wherein the control unit is configured to control such that dispensing is continued if the dispensing is performed for calibration (CAL) or control (CTL) even when the cumulative count exceeds the threshold value.

7. The automatic analysis apparatus according to claim 1, wherein the control unit is configured to use a count value set and stored in advance or a count value set from a graphical user interface (GUI) as the count value.

8. A cleaning method for an automatic analysis apparatus including:
a dispensing mechanism including a probe configured to dispense a sample or a reagent into a reaction container;
a cleaning mechanism configured to clean the probe; and a control unit configured to control the dispensing mechanism and the cleaning mechanism,
wherein the control unit obtains, on the basis of count values indicating weightings to contamination and corresponding to a plurality of analysis conditions, a cumulative count obtained by accumulating the count values for each dispensing of the sample or the reagent, where the analysis conditions include information on contamination ranges both inside and outside the probe, and controls the cleaning mechanism to clean the probe when the cumulative count exceeds a set threshold value.

9. The cleaning method for an automatic analysis apparatus according to claim 8,
wherein the analysis item includes colorimetry, ISE and HbA1c.

10. The cleaning method for an automatic analysis apparatus according to claim 9,
wherein the analyte type includes serum, plasma, urine, spinal fluid, whole blood and blood cells.

11. The cleaning method for an automatic analysis apparatus according to claim 9,
wherein the dispensing operation includes suction from a liquid surface or a bottom surface of a sample container.

12. The cleaning method for an automatic analysis apparatus according to claim 8,
wherein the control unit is configured to use a count value set and stored in advance or a count value set from a GUI as the count value.

13. The automatic analysis apparatus according to claim 1, wherein the information on the contamination ranges both inside and outside the probe include information on a dispensing operation determined based on an analysis item and an analyte type.

14. The automatic analysis apparatus according to claim 1,
wherein the analysis conditions include information on an alarm.

15. The automatic analysis apparatus according to claim 13,
wherein the analysis item includes colorimetry, ISE, and HbA1c.

16. The automatic analysis apparatus according to claim 13,
wherein the analyte type includes serum, plasma, urine, spinal fluid, whole blood and blood cells.

17. The automatic analysis apparatus according to claim 13,
wherein the dispensing operation includes suction from a liquid surface or a bottom surface of a sample container.

18. The cleaning method for an automatic analysis apparatus according to claim 8,
wherein the analysis conditions include a dispensing operation.

19. The cleaning method for an automatic analysis apparatus according to claim 8,
wherein the information on the contamination ranges both inside and outside the probe include information on a dispensing operation determined based on an analysis item and analyte type.

20. The cleaning method for an automatic analysis apparatus according to claim 8,
wherein the analysis conditions include information on a cleaning method for the probe.

21. The cleaning method for an automatic analysis apparatus according to claim 19,
wherein the analysis item includes colorimetry, ISE and HbA1c.

22. The cleaning method for an automatic analysis apparatus according to claim 19,
wherein the analyte type includes serum, plasma, urine, spinal fluid, whole blood and blood cells.

23. The cleaning method for an automatic analysis apparatus according to claim 18,
wherein the dispensing operation includes suction from a liquid surface or a bottom surface of a sample container.

24. The cleaning method for an automatic analysis apparatus according to claim 8,
wherein the control unit is configured to use a count value set and stored in advance or a count value set from a GUI as the count value.

* * * * *